United States Patent [19]
Davis et al.

[11] Patent Number: 6,033,373
[45] Date of Patent: Mar. 7, 2000

[54] ORTHOPAEDIC KNEE BRACE

[75] Inventors: Peter Ian Davis, Sunbury-on-Thames; Kenneth Paul Davis, High Wycombe, both of United Kingdom

[73] Assignee: Directaid Limited, United Kingdom

[21] Appl. No.: 09/053,011

[22] Filed: Apr. 1, 1998

[30] Foreign Application Priority Data

Apr. 1, 1997 [GB] United Kingdom .................. 9706584

[51] Int. Cl.[7] ...................................... A16F 5/00
[52] U.S. Cl. ................................. 602/26; 602/16
[58] Field of Search ................ 602/16, 26, 20; 623/57.59

[56] References Cited

U.S. PATENT DOCUMENTS

| | | | |
|---|---|---|---|
| 2,594,227 | 4/1952 | Smith | 602/16 |
| 5,000,169 | 3/1991 | Swicegood et al. | 602/26 |
| 5,460,599 | 10/1995 | Davis et al. | 602/26 |
| 5,672,152 | 9/1997 | Mason et al. | 602/26 |

Primary Examiner—Richard J. Apley
Assistant Examiner—Jayne Saydah
Attorney, Agent, or Firm—Watson Cole Grindle Watson, P.L.L.C.

[57] ABSTRACT

The present invention provides a hinge for an orthopaedic knee brace comprising first and second hinge members rotatably connected together. The first hinge part is provided with an annular slot for receiving a pin provided on the second hinge member. First and second stop members are provided with opposed stop faces located in the region of the annular slot and are manually positionable circumferentially along the annular slot whereby to define a limited range of relative movement between the hinge members and a clamping member is provided for applying a clamping force to the stop members in a direction parallel to the axis of rotation of the hinge members, the stop members and the first hinge member having inter-engaging projections and recesses whereby to clamp the stop members to the first hinge member.

7 Claims, 4 Drawing Sheets

ORTHOPAEDIC KNEE BRACE

BACKGROUND OF THE INVENTION

The present invention relates to an orthopaedic knee brace and more particularly to the construction of a hinge in such a brace.

Orthopaedic knee braces are commonly used during rehabilitation following either injury or surgery and normally include two adjustable hinges, one on either side of a braced knee. Knee braces serve two purposes. Firstly, the brace has to support the knee at all times but especially during movement Secondly, the brace should limit knee movements in flexion or extension within limits beyond which injury to the knee may occur.

Flexion is defined as flexing of the knee from the extended position to a position where the foot and ankle is bent towards the thigh. Extension is defined as being the opposite movement. An extended leg is normally straight with virtually no bending at the knee joint.

Knee braces have been the subject of much design attention and examples of previous proposals are described in U.S. Pat. Nos. 4,088,130; 4,340,041; 5,052,379; 5,107,824 and 5,460,599. The fundamental problem is that each binge has to be capable of being adjusted through a relatively wide range of limits of flexion and extension so as to be able to cater for various different patients and their separate requirements. In the past this has resulted in either very complicated adjustment procedures or in arrangements which cannot reliably maintain the limiting positions. There is thus still a need to provide a hinge for an orthopaedic knee brace which is simple in construction, easy to use and yet reliably maintains the limiting positions for flexion and extension.

SUMMARY OF THE INVENTION

The present invention provides a hinge for an orthopaedic knee brace comprising first and second hinge members rotatably connected together. The first hinge part is provided with an annular slot for receiving a pin provided on the second hinge member. First and second stop members are provided with opposed stop faces located in the region of the annular slot and are manually positionable circumferentially along the annular slot whereby to define a limited range of relative movement between the hinge members and a clamping member is provided for applying a clamping force to the stop members in a direction parallel to the axis of rotation of the hinge members, the stop members and the first hinge member having inter-engaging projections and recesses.

The inter-engaging projections and recesses may engage in a plane parallel to the plane of the first hinge member. Alternatively, the stop members may be received in an upstanding portion of the first hinge member with the upstanding portion of the hinge member and the peripheries of the stop members forming the inter-engaging projections and recesses in an annular fashion parallel to the axis of rotation of the hinge.

Preferably, the clamping forces are provided by a rotatable wedge member, the wedge member being rotatable through an angle of less than 180° and preferably only 90° in order to create the wedging effect.

BRIEF DESCRIPTION OF THE DRAWINGS

In order that the present invention be more readily understood, embodiments therefore will now be described by way of example with reference to the accompanying drawing, in which.

DETAILED DESCRIPTION OF THE PREFERRED EMBODIMENT

Figure 1:
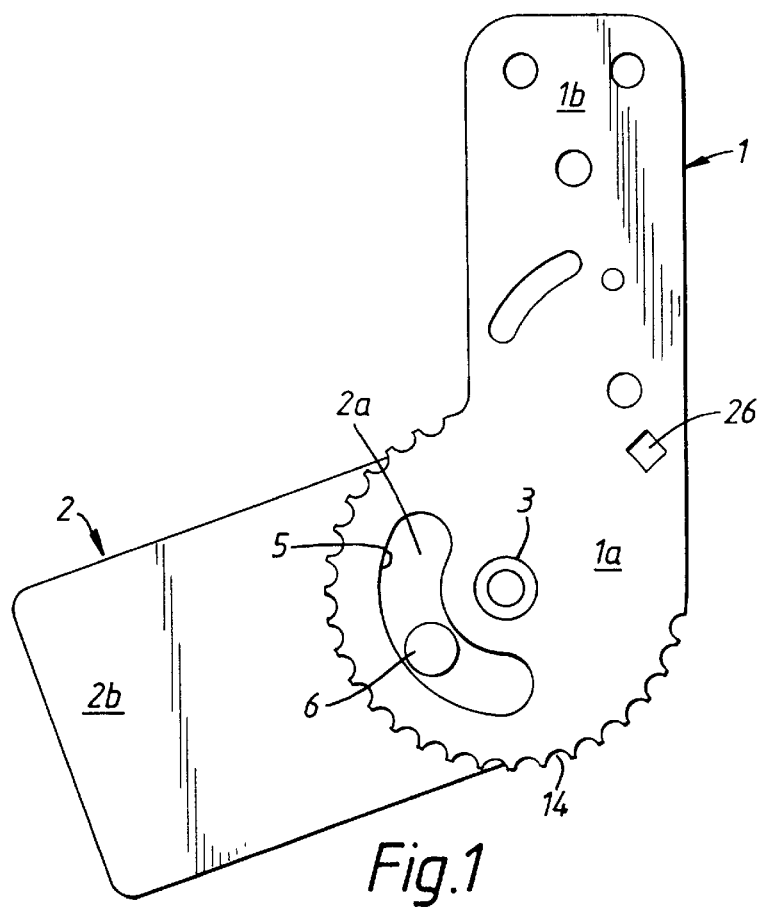
FIG. 1 is a perspective view of a part of a hinge according to the present invention.

As shown in FIG. 1, a hinge for an orthopaedic rehabilitation knee brace comprises first and second hinge members 1, 2 pivotally connected together for relative movement about a post 3. Each hinge member is a generally flat plate made of metal and has a generally circular portion 1a, 2a with relatively straight portions 1b, 2b extending therefrom. These straight portions are adapted for connection to members which will be attached to the calf and thigh so as to provide the necessary connection to the leg.

In order to limit the amount of movement of the hinge, and, indeed, to ensure that the movement in flexion is in the correction direction, an arcuate slot 5 is provided in the hinge member 1 and receives a pin 6 fixed to the hinge member 2. The extent of the slot 5 determines the maximum flexure available from the hinge.

Figure 2:
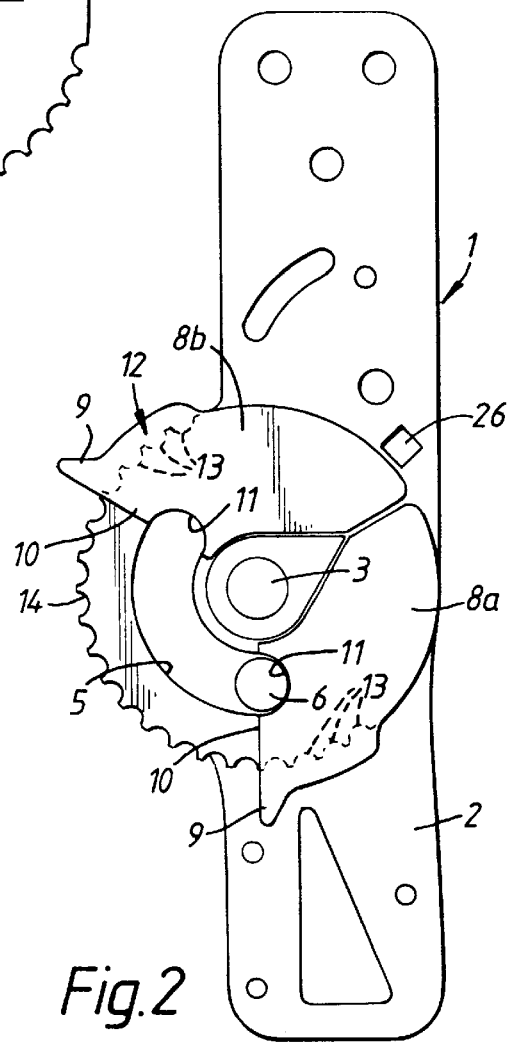
FIG. 2 is a perspective view of another part of the hinge according to the present invention for use with the part shown in FIG. 1.

If one now refers to FIG. 2, this shows two movable locking plates 8a, 8b mounted for movement about the post 3. Each plate 8 is generally sector shaped with ears 9 which enable the plates to be manually rotated to any desired position. Facing radial edges 10 are provided with arcuate recesses 11 at positions in register with the slot 5. The separation between the edges 10 of the plates 8 determines the amount of flexure while the actual position of the plate 8a determines the extension.

The plates 8 are fixed in the desired position with respect to the hinge member 1 by means of inter-engaging projections and recesses between a portion of each plate 8 and the hinge member 1. In this embodiment the plates 8 are provided with an arcuate section 12 provided with radially inwardly projecting protrusions 13 which are shown to be half round in cross section. The protrusions 13 are arranged to mate with radially outwardly directed protrusions 14 provided on the hinge member 1. In this embodiment the protrusions 14 are formed around the periphery of the circular portion 1a of the hinge member 1 using a stamping process. In order to adjust the limits of flexion and extension it is necessary to allow the locking plates 8 to move around the post 3. It is consequently necessary to disengage the projections 13 from the projections 14. In this embodiment this is achieved by allowing the plates 8 to move axially along the post 3 under the action of a spring, 35 and shown in FIG. 3, whereupon it is then possible to rotate one or both plates 8 to a new position and then by pressing the plates against the action of the spring 35 bring the projections 13 and 14 back into engagement in a new angular position of the plates with respect to the hinge member 1.

The mechanism by which this axially directed force can be applied will now be described in relation to FIG. 3, which shows an exploded perspective view of an adjustment assembly arranged to be mounted on the post 3 on one side of the hinge. The adjustment assembly consists of an upper carrier member 20 provided with means defining a bore 21 which receives the post 3 and is a sliding fit thereon. The locking plates 8a, 8b are rotatably mounted onto the means defining the bore 21 such that the manually operable ears 9 project beyond periphery of the plate 20. When mounted on the post 3, the assembly is capable of sufficient axial movement along the post 3 to permit engagement and disengagement of the projections 13 and 14. The outer surface of the member 20 is provided with one or more ramps 22 which are arranged to engage with a rotatably mounted cam member 29 on the end of the post 3. Arcuate movement of the cam member is thus translated by the ramp and cam into axial movement of the assembly along the post 3 in order to clamp the locking plates 8a and 8b into the desired position. Depending upon the material chosen to form the carrier member 20 and the plates 8a and 8b, it may be necessary to provide a reinforcing plate to transfer the force from the member 20 onto the locking plates 8a and 8b.

The adjustment assembly of the carrier member 20 and locking plates 8a,8b is such that even if the assembly is removed from the post 3, the plates are retained on the means defining the bore 21 thus keeping the number of separate parts to a minimum.

The cam member 29 should have a pair of ramp surfaces corresponding to those surfaces 22 on the member 20. The lengths and disposition of the ramps is such that angular movement to the cam member through less than 180° and preferably 90° is all that is required in order to clamp the plates 8a and 8b in the desired position on the hinge member.

Figure 3:
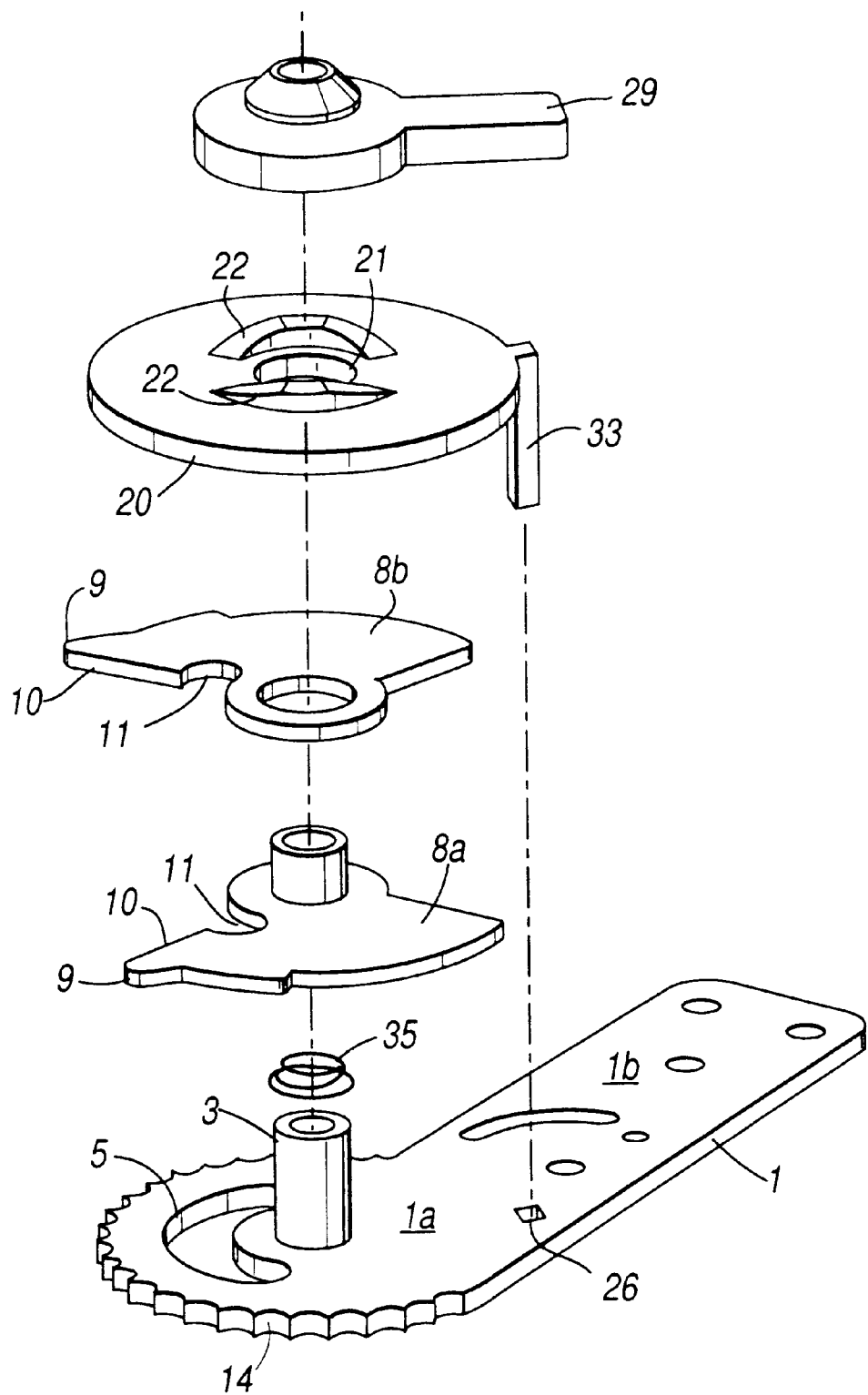
FIG. 3 is an exploded perspective view of an adjustment assembly in accordance with a embodiment of the present invention.
Figure 4:
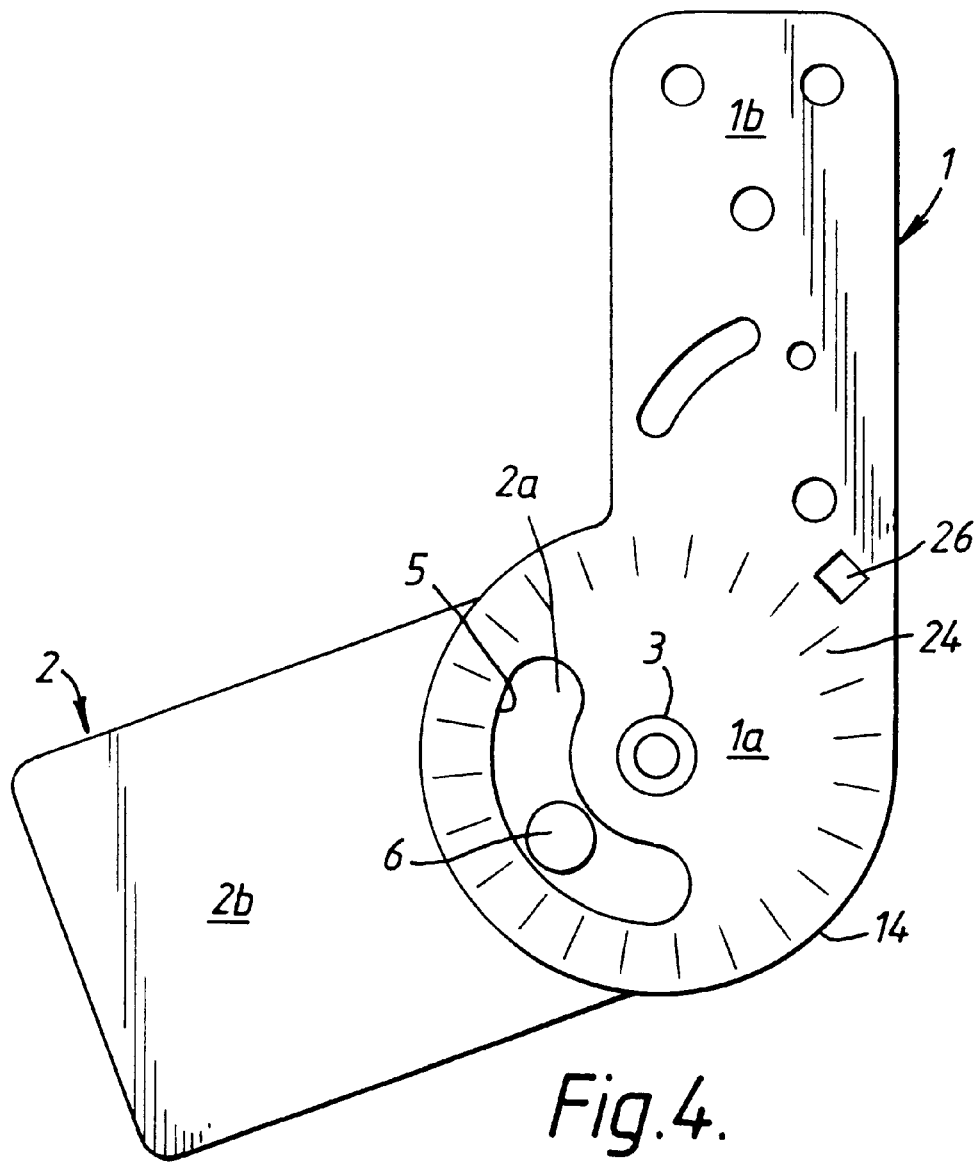
FIG. 4 is a perspective view similar to that shown in FIG. 1 but of a second embodiment of the present invention.
Figure 5:
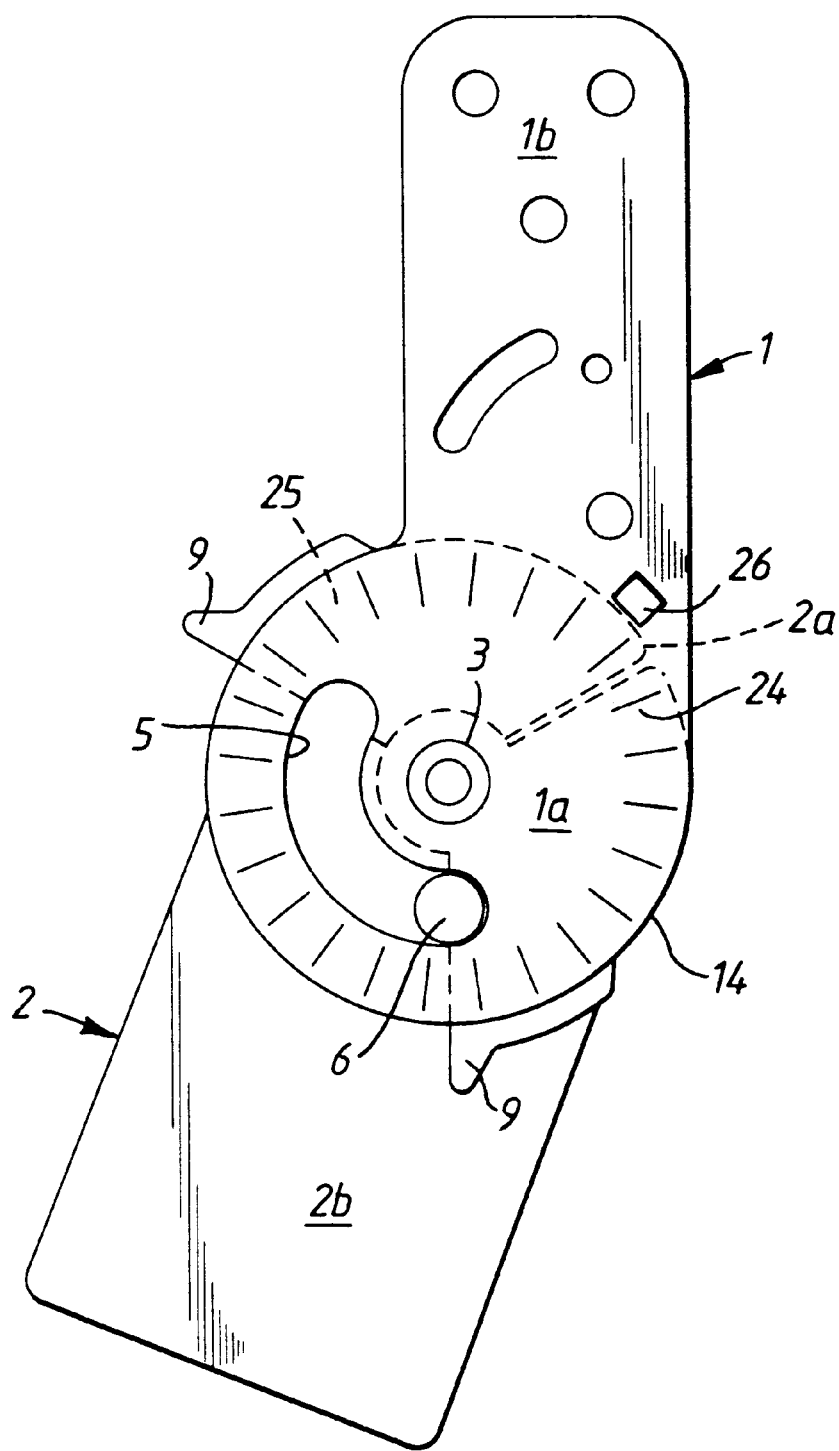
FIG. 5 is a perspective view of another part of the second embodiment of the present invention.

FIGS. 4 and 5 show an alternative embodiment which by and large is similar in construction and function to the embodiment described in relation to FIGS. 1 to 3 and the same reference numerals are applied to the same parts. Here the inter-engaging projections and recesses are formed in the plane of the hinge members rather than parallel to the post 3. As will be seen from FIG. 4, there is a circular array of stamped recesses 24 in the surface of the hinge member 1 which are arranged to receive corresponding stamped projections 25 in the locking plates. This arrangement is simpler than the arrangement described in relation to FIGS. 1 to 3 in that there is no need to provide the spring in order to create axial movement of a substantial amount along the post 3. The projections and recesses 24 and 25 are relatively shallow and the degree of movement required from the adjustment assembly utilizing the member 20 and camming arrangement is usually sufficient to permit the plates to be slid over the hinge 1 using the ears 9. However, the amount of force which can be applied axially in order to keep the plates 8 in the desired position can be quite large in order to ensure that the plates 8 do not move during use.

Both the above arrangements have the advantage that the relative positions of the plates 8 can be readily adjusted by virtue of the arcuate movement of the cam bearing member. However, once in the desired, adjusted position, the plates are held securely.

Various modifications may be made to the above arrangements and in particular a suitable lock arrangement could be added to lock the hinge in any desired position eg straight or with a fixed degree of flection. Also, the periphery of the carrier member 20 is preferably provided with marks indicative of the angle between the two hinge member from 0° to 120° in steps of 10°. The size and spacing of the projections and recesses on the plates 8 and hinge member 1 are chosen to be compatible with this. This, in turn requires the adjustment assembly to be fixed in position on the hinge member 1. We propose to fix the adjustment assembly in position by means of a tongue 33 shown in FIG. 3 which is fixed to the assembly at a predetermined position and is received in an aperture 26 shown-in FIGS. 1 and 2 in the hinge member 1. The tongue is long enough to remain in the aperture 25 during the clamping and release modes of operation.

What is claimed is:

1. An orthopaedic knee brace comprising first and second hinge members interconnected for pivotal movement about an axis, the first hinge member being provided with an arcuate slot receiving a pin provided on the second hinge member, a pair of locking plates pivotally mounted on said axis, said plates having opposing arcuate recesses located in the region of the arcuate slot and being manually positionable whereby to define a limited range of relative movement between the hinge members and interengaging means provided on said plates and said first hinge member for fixing said plates to a desired position, said interengaging means extending in a direction parallel to said axis requiring said plates and said first hinge member to be relatively shifted in said direction for fixing said plates to the desired position.

2. An orthopaedic knee brace according to claim 1, wherein said interengaging means comprise inter-engaging projections and recesses on said plates and said first hinge member.

3. An orthopaedic knee brace according to claim 2, wherein said recesses are provided in a peripheral position of said first hinge member, and said projections are provided on arcuate sections of said locking plates.

4. An orthopaedic knee brace according to claim 1, wherein the locking plates each comprise a wedge shaped member mounted for rotation about the pivotal axis.

5. An orthopaedic knee brace according to claim 4, wherein each said locking plate is rotatable through an angle of less than 180°.

6. An orthopaedic knee brace according to claim 5, wherein each said locking plate is rotatable through an angle of less than 90°.

7. An orthopaedic knee brace according to claim 1, wherein each said locking plate is provided with manually actuable ears extending beyond the general profile of the first hinge to permit movement of the locking plates.

* * * * *